United States Patent [19]

van der Jagt

[11] Patent Number: Plant 6,037

[45] Date of Patent: Oct. 13, 1987

[54] CHRYSANTHEMUM

[75] Inventor: Martinus van der Jagt, Ter Aar, Netherlands

[73] Assignee: Chrysanthemum Breeders Association, N.V., Curacao, Netherlands Antilles

[21] Appl. No.: 698,593

[22] Filed: Feb. 4, 1985

[51] Int. Cl.[4] ..... A01H 5/00

[52] U.S. Cl. ..... Plt./76

[58] Field of Search ..... Plt./76

*Primary Examiner*—Robert E. Bagwill

*Attorney, Agent, or Firm*—Parkhurst & Oliff

[57] ABSTRACT

A new and distinct cultivar of Chrysanthemum plant named 'Blue Redemine', bearing medium sized violet-red blooms with a red center and having a performance of twenty days.

3 Drawing Figures

BACKGROUND OF THE NEW PLANT

The new plant of the present invention relates to the Chrysanthemum genus.

ORIGIN AND HISTORY OF THE PLANT

The new plant according to the present invention comprises a new and distinct cultivar of Chrysanthemum plant which is a colormutant of Chrysanthemum named 'Redemine'. The new cultivar was discovered by Martinus van der Jagt in 1982 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and violet-red color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Figure 1:
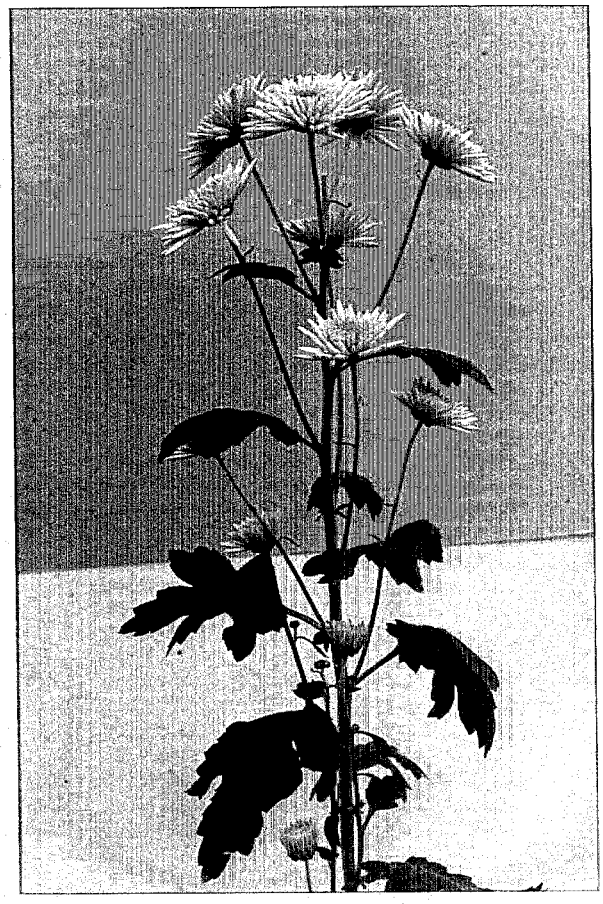
Figure 2:
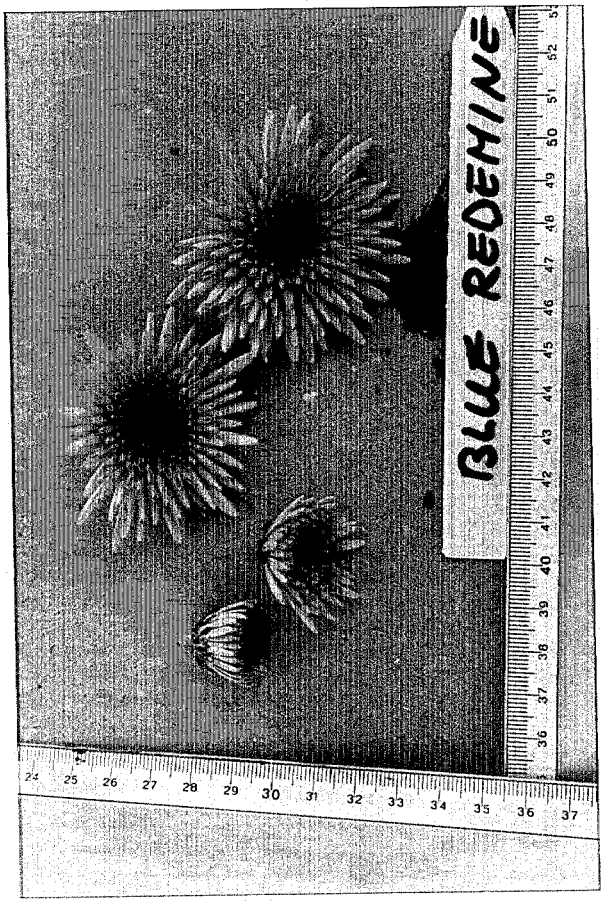
Figure 3:
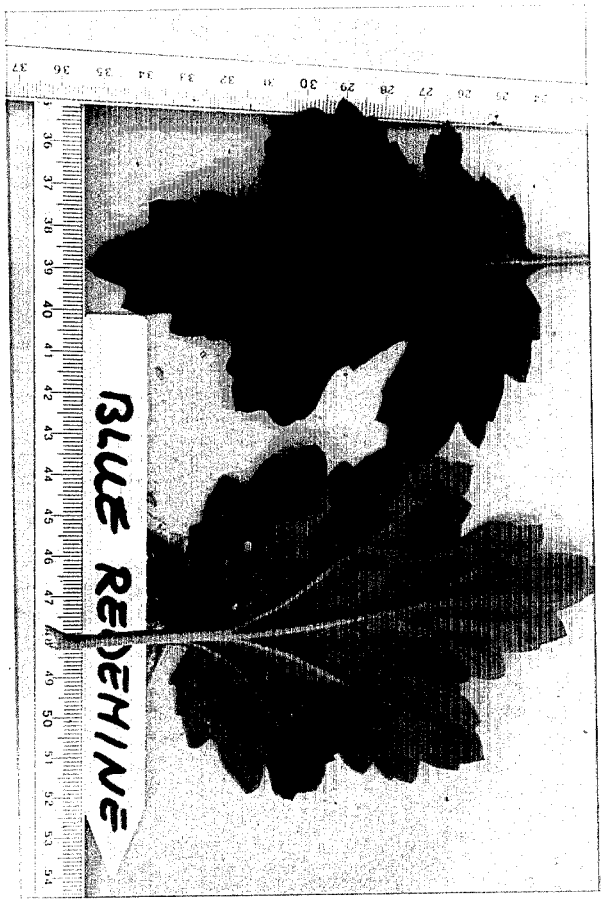

Sheet 2 shows various stages of bloom of the new cultivar; and

Sheet 3 shows the foliage and petiole of the new cultivar.

DESCRIPTION OF THE NEW PLANT

This new variety of Chrysanthemum is of the botanical classification *Chrysanthemum morifolium*, named 'Blue Redemine'. When grown in the vicinity of Ter Aar, Holland, it has a response time of approximately ten and one-half weeks. This new variety produces medium sized violet-red blooms with a red center having a performance of twenty days. This new variety of Chrysanthemum has been found to retain its distinctive characteristics throughout successive propagations and may be planted under conventional greenhouse conditions in Holland.

The following is a description of the plant and characteristics that distinguish it over related known varieties and its antecedents:

Botanical classification: *Chrysanthemum morifolium.*

Bud:
- *Size.*—Medium, cross sect. 1.5 cm, height 1.3 cm. approx.
- *Form.*—Round and high.
- *Color.*—Rhodonite Red R.H.S. 0022/1.

Bloom:
- *Size.*—Medium.
- *Fully expanded.*—6–7 cm.
- *Borne.*—Single.
- *Stems.*—Strong (thick).
- *Forms.*—Multiple short, tubular petals.
- *Permanence.*—Good, 20 days (at 18°–20° C.

Color:
- *Center of flower (disk floret).*—Red R.H.S. 0022.
- *Base of petals.*—Red, R.H.S. 0022.
- *Inside of petals.*—Red, R.H.S. 025/2.
- *Reverse of petals.*—Red, R.H.S. 025/2.
- *Outer petals.*—Red, R.H.S. 025/3.
- *Tonality from a distance.*—Small decorative with tubular petals of violet-red color.
- *Discoloration.*—To a more pale type of red R.H.S. (spinel pink) 0625/3.

Petals:
- *Texture (upper and underside).*—Rough, petals are hard and thick.
- *Number.*—In excess of 150 including center.
- *Cross-section.*—Tubular.
- *Arrangement.*—Imbricated (decorative).
- *Persistance.*—Strong, petals do not reflex at all.
- *Fragrance.*—Normal for Chrysanthemum.

Reproductive organs:
- *Stamen.*—Small.
- *Pollen.*—Do not appear when blooming.
- *Styles.*—Thin, columnar.
- *Length.*—Medium, 7 mm long.
- *Stigmas.*—Very small. Green (R.H.S. 61/2) width — 0.5 mm. approx.
- *Ovaries.*—Enclosed in calyx.

Plant:
- *Form.*—Single stem spray, meant for erect culture.
- *Growth.*—Vigorous.
- *Height.*—Tall, approx. 105 cms.
- *Peduncle.*—Strong. Near the top — 7 cms. In the Middle — 14 cms. Near the Bottom — 20 cms.
- *Internodes.*—3½ cm.
- *Flowering response.*—10½ weeks.

Foliage:

*Color.*—R.H.S. 000858.
*Size.*—Width 8½ cm., length 11 cm.
*Quantity.*—Between 28–32.
*Shape.*—Oval, undulated.
*Texture.*—Leaves are soft and feel smooth. Upperside: Smooth, heavy layer of hair. Underside: Smooth, heavy layer of hair.
*Ribs and veins.*—Developed in normal quantity. Upperside: Ribs pronounced, veins very fine. Underside: Ribs pronounced, veins very fine.
*Edge.*—Undulated.
*Leaf Underside.*—Smooth, heavy layer of hair.

In the description above, color references are made to the "Horticultural Colour Chart I & II" issued by the British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinct cultivar of Chrysanthemum named 'Blue Redemine', as described and illustrated in the foregoing specification and accompanying drawings.

* * * * *